US012022785B2

(12) United States Patent
Miyako (10) Patent No.: US 12,022,785 B2
(45) Date of Patent: Jul. 2, 2024

(54) POLLEN SUPPLYING METHOD

(71) Applicant: Japan Advanced Institute of Science and Technology, Ishikawa (JP)

(72) Inventor: Eijiro Miyako, Ishikawa (JP)

(73) Assignee: JAPAN ADVANCED INSTITUTE OF SCIENCE AND TECHNOLOGY (JP)

(*) Notice: Subject to any disclaimer, the term of this patent is extended or adjusted under 35 U.S.C. 154(b) by 460 days.

(21) Appl. No.: 17/275,841

(22) PCT Filed: Nov. 12, 2019

(86) PCT No.: PCT/JP2019/044444
§ 371 (c)(1),
(2) Date: Mar. 12, 2021

(87) PCT Pub. No.: WO2020/105518
PCT Pub. Date: May 28, 2020

(65) Prior Publication Data
US 2022/0039343 A1  Feb. 10, 2022

(30) Foreign Application Priority Data
Nov. 19, 2018 (JP) ................... 2018-216647

(51) Int. Cl.
*A01H 1/02* (2006.01)
(52) U.S. Cl.
CPC .................... *A01H 1/027* (2021.01)
(58) Field of Classification Search
USPC ........................................................ 47/1.41
See application file for complete search history.

(56) References Cited

U.S. PATENT DOCUMENTS

2016/0353661 A1* 12/2016 Caldeira ............... A01H 1/027

FOREIGN PATENT DOCUMENTS

| CN | 107306787 | * | 11/2017 | ............... A01H 1/02 |
| CN | 107306787 A | | 11/2017 | |
| CN | 107364578 | * | 11/2017 | ............... H02J 7/35 |
| JP | 2003525884 A | | 9/2003 | |
| JP | 2006246702 | * | 9/2006 | ............... A01H 1/02 |
| JP | 2006246702 A | | 9/2006 | |
| JP | 2009178083 A | | 8/2009 | |
| JP | 2010275252 A | | 12/2010 | |
| JP | 2011200196 | * | 10/2011 | ............... A01G 7/06 |

(Continued)

OTHER PUBLICATIONS

Balloon pollination gives date growers a bigger bang for the buck, ABC Rural / Caddie Brain, Posted Mon Dec. 10, 2012 at 1:36am, updated Mon Dec. 10, 2012 at 5:04pm, [retrieved from internet Sep. 5, 2023 https://www.abc.net.au/news/rural/2012-12-10/balloon-pollination-gives-date-growers-a-bigger/6152310] 2 pages.*

(Continued)

*Primary Examiner* — Andrea M Valenti
(74) *Attorney, Agent, or Firm* — MASCHOFF BRENNAN (57) ABSTRACT

A pollen supplying method for supplying pollen to a pistil of a plant includes an air bubble production step of producing an air bubble with the pollen attached to the surface thereof, and an air bubble attachment step of releasing the produced air bubble into the air and attaching the air bubble to the pistil.

10 Claims, 8 Drawing Sheets

(56) References Cited

FOREIGN PATENT DOCUMENTS

| | | | |
|---|---|---|---|
| JP | 2017012137 | A | 1/2017 |
| JP | 2018014929 | A | 2/2018 |

OTHER PUBLICATIONS

Yokota, Comparison of salt tolerance in pollen tubes between Camellia japonica and C. sinensis, Soil Science and Plant Nutrition, 36(1), 145-148, Mar. 1990; DOI: 10.1080/00380768.1990.10415719.

* cited by examiner

POLLEN SUPPLYING METHOD

CROSS REFERENCE TO RELATED APPLICATIONS

This application is a national phase of International Patent Application No. PCT/JP2019/044444, filed Nov. 12, 2019, which claims priority to Japanese Patent Application No. 2018-216647, filed Nov. 19, 2018, all of which are incorporated by reference herein in their entirety.

TECHNICAL FIELD

The present disclosure relates to a pollen supplying method for supplying pollen to a pistil of a plant.

BACKGROUND ART

Known examples of a pollen supplying method for supplying pollen to a pistil of a plant in fruit growing, horticulture, and the like include a method of causing insects such as honeybees to mediate pollination. However, the method requires insect management, and in addition, when the method is performed outdoors, control of directing insects to pollination of a specific plant is difficult. Therefore, a method of supplying pollen by a human or a machine is required.

Patent Literature 1 discloses an artificial pollination method of a human spraying a dispersion acquired by dispersing pollen in a specific liquid agent. Viscosity of the dispersion is adjusted by mixing an ether-based agent enhancing dispersibility of pollen along with sucrose, sorbitol, and the like increasing the germination rate of the pollen and elongation of the pollen tube and further adding peach resin; and attachability of the dispersion to a stigma of a pistil is enhanced by the viscosity adjustment.

Patent Literature 2 discloses a method of discharging pollen or a suspension of pollen to a part to be pollinated on a plant from a rotor-blade type unmanned flying object provided with an injection nozzle. The method suppresses scattering of the pollen or the suspension by generating a swirling air current around a plant cultivated indoors by an air blowing mechanism of the unmanned flying object.

CITATION LIST

Patent Literature

Patent Literature 1: Unexamined Japanese Patent Application Publication No. 2010-275252
Patent Literature 2: Unexamined Japanese Patent Application Publication No. 2017-12137

SUMMARY OF INVENTION

Technical Problem

The methods disclosed in Patent Literature 1 and 2 require high injection pressure in order to accurately inject a dispersion in which pollen is dispersed toward a plant. In particular, when a dispersion is injected by a rotor-blade type unmanned flying object as is the case in Patent Literature 2, the unmanned flying object needs to fly at a certain distance from a plant in such a way as not to damage the plant by an air current generated by the flight, and high injection pressure is required in order for the dispersion to pass through the air current and reach the plant. Therefore, the methods disclosed in Patent Literature 1 and 2 have a problem that a dispersion injected at high injection pressure drops a flower and damages a pistil. Consequently, the methods disclosed in Patent Literature 1 and 2 may result in incomplete pollination and even when pollination is complete, may result in malformation of a borne fruit.

The present disclosure has been made in view of the aforementioned actual circumstances, and an objective of the present disclosure is to provide a pollen supplying method that can efficiently supply pollen to a pistil of a plant even when an unmanned flying object such as a drone is used.

Solution to Problem

In order to achieve the aforementioned objective, a pollen supplying method according to the present disclosure is a pollen supplying method for supplying pollen to a pistil of a plant and includes:
  an air bubble production step of producing an air bubble with the pollen attached to a surface thereof; and
  an air bubble attachment step of releasing the produced air bubble into air and attaching the air bubble to the pistil.

The air bubble may be a sphere with a diameter of any length.

An aqueous solution used for producing the air bubble may contain a surface-active agent.

An aqueous solution used for producing the air bubble may contain a thickener raising viscosity.

An aqueous solution used for producing the air bubble may contain a substance activating germination of the pollen and elongation of a pollen tube.

The aqueous solution may be added with at least sucrose, boric acid, magnesium sulfate, calcium chloride, potassium chloride, and gelatin.

The air bubble production step may produce the air bubble with the pollen attached to a surface thereof when releasing the air bubble by the air bubble attachment step, and
  the pollen may be preserved in a powdery state until being attached to a surface of the air bubble.

The air bubble production step may produce the air bubble with the pollen attached to a surface thereof, by bringing the pollen into contact with an air bubble without the pollen attached to a surface thereof.

The air bubble production step may produce the air bubble with the pollen attached to a surface thereof, by bringing an air bubble without the pollen attached to a surface thereof into contact with the pollen.

The air bubble may burst by water given by the pistil.

The air bubble attachment step may release the air bubble by use of an unmanned flying object.

Advantageous Effects of Invention

The present disclosure enables pollination with a less amount of pollen compared with a case of injecting an aqueous solution in which pollen is dispersed, by an air bubble released into the air coming into contact with a pistil, and enables supply of pollen without damaging a pistil. Consequently, pollen can be efficiently supplied to a pistil of a plant even when an unmanned flying object such as a drone is used.

DESCRIPTION OF EMBODIMENTS

An embodiment of the present disclosure will be described in detail with reference to drawings. A pollen supplying method according to the embodiment first produces an aqueous solution in which pollen of a plant to be pollinated is dispersed by adding the pollen and a surface-active agent to water and then produces an air bubble of the aqueous solution. In other words, pollen is attached to the surface of the air bubble. Then, the pollen supplying method releases the produced air bubble into the air and attaches the air bubble to a pistil of the plant to be pollinated. For example, soap bubbles are formed from the aqueous solution in which the pollen is dispersed and are sprayed into the air in such a way as to attach to pistils. For example, a commercially available soap bubble maker can be used for production and spraying of air bubbles.

In the pollen supplying method according to the embodiment, an aqueous solution for producing air bubbles contains a thickener, and thus viscosity is increased. For example, the thickener may be polyvinyl alcohol (PVA) or may be any one item of sugar, honey, gelatin, and starch powder that are of natural origin. An air bubble becomes more likely to burst by dispersing pollen in an aqueous solution; however, strength of the air bubble is increased by the thickener and therefore the bubble becomes less likely to burst even when pollen is dispersed in the aqueous solution. Consequently, the time until a burst of an air bubble becomes longer, and the probability of the air bubble coming into contact with a pistil increases.

Specifically, as the time of an air bubble floating in the air without bursting becomes longer, the floating distance of the air bubble becomes longer, and opportunities of the air bubble coming into contact with a pistil or a petal increases. Further, an air bubble being in contact with a petal may move over the petal and come into contact with the pistil, and therefore opportunities of coming into contact with the pistil increases as the time until a burst becomes longer. Further, pollen may move over an air bubble, come into contact with a stigma, and complete pollination without a burst of the air bubble as long as the air bubble is in contact with the pistil. Thus, the pollen supplying method according to the embodiment can increase the probability of an air bubble coming into contact with a pistil and, by extension, the probability of pollination by using a thickener and, as a result, can reduce an amount of pollen to be used.

A test for measuring strength of an air bubble produced from an aqueous solution containing a thickener was performed, and the air bubble did not burst merely by being placed on a glass substrate and was robust to the extent that compressive stress could be measured by a compression tester, as illustrated in FIGS. 1 and 2. Compressive stress was acquired by measurement and analysis by a uniaxial compression test at a speed of 5 mm/min using a precision universal tester (AG-100kNX manufactured by Shimadzu Corporation), the test being outsourced to UBE Scientific Analysis Laboratory, Inc.

In the measurement and testing, in order to produce an aqueous solution for forming an air bubble, 5 mL of sodium polyoxyethylene lauryl ether sulfate (EMAL E-27C manufactured by Kao Corporation) as a surface-active agent and 19 g of polyvinyl alcohol (mean degree of polymerization: approximately 1500, manufactured by FUJIFILM Wako Pure Chemical Corporation) as a thickener were first added to 150 mL of distilled water, the mixture was stirred for five hours at room temperature by use of a stirrer, and then microbubbles were removed by leaving the mixture at rest for one night; and thus a soap bubble solution was produced.

Pollen was taken out from a lily flower along with an anther, was dried for one night by a thermostat adjusted to 25° C., and then was isolated from the anther by stirring with acetone; and after removal of the anther, five-minute acetone cleaning by centrifugation at 1000 rpm was performed three times and the pollen was acquired as a pellet. An aqueous solution in which pollen is dispersed was produced by dispersing 50 mg of the acquired pellet in 1 mL of distilled water and mixing the dispersion with 4 mL of the soap bubble solution described above.

As illustrated in FIG. 2, some of air bubbles formed by the thus produced aqueous solution exhibit a maximum uniaxial compression value of approximately 13 mm, and a maximum compressive stress of approximately 0.04 N was measured.

Further, when an air bubble formed by the thus produced aqueous solution was placed on a glass substrate and was observed with an optical microscope, a state of pollen being dispersed in the aqueous solution was observed as illustrated in FIG. 3.

Further, a pistil secretes moisture from the stigma when an air bubble comes into contact with the pistil, and therefore an aqueous solution forming the air bubble in contact is given moisture. Therefore, moisture of the aqueous solution of the air bubble in contact with the pistil increases, and viscosity of the aqueous solution decreases. Consequently, the air bubble is more likely to burst and bursts by moisture being continuously given from the pistil, and the aqueous solution in which pollen is dispersed is sprayed in close proximity to the pistil. Consequently, the pollen supplying method according to the embodiment can spray the aqueous solution in close proximity to the pistil. At this time, a part of the aqueous solution not directly in contact with the pistil in the air bubble in contact with the pistil may contribute to pollination. For example, when the air bubble bursts in such a way as to be drawn to a part in contact with the stigma, most of the aqueous solution forming the air bubble comes into contact with the stigma, and most of pollen contained in the air bubble acquires an opportunity to come into contact with the stigma.

When actual states of air bubbles attaching to pistils and then bursting were checked, an air bubble attaching to a pistil of an azalea burst approximately after one minute, as illustrated in FIG. 4A, whereas an air bubble attaching to a pistil of a campanula burst approximately after five minutes, as illustrated in FIG. 4B. It is assumed that the reason the air bubble attaching to the pistil of the azalea burst earlier is that the stigma of the pistil of the azalea is larger than and holds a larger amount of moisture than that of the campanula and therefore gave a larger amount of moisture to the air bubble. Further, it was confirmed in a case of a lily having a yet larger stigma than the azalea that the time between attachment and a burst was about 10 seconds. As a result, it was found that a stigma with a greater amount of moisture bursts an air bubble earlier.

Further, in order to check a state of a pistil after pollination, a pistil of a lily flower, the stigma of which was hit by a soap bubble formed of an aqueous solution in which pollen was thus dispersed, was left at rest for one night and the stigma thereof was observed. In the observation, first, the stigma was heated for one hour by a 1 N aqueous sodium hydroxide solution (a 1 mol/l aqueous sodium hydroxide solution) at 60° C. and stained by an aqueous aniline blue solution; and an observation preparation was prepared by placing a section of the stigma between two cover glasses. The preparation was observed with a fluorescence microscope (IX73 manufactured by Olympus Corporation) equipped with an object lens with magnifying power of 60 (UPLFLN60X manufactured by Olympus Corporation). The stamen of the flower used for the observation was previously removed in order to eliminate an effect of self-pollination. As a result of the observation, formation of a pollen tube was confirmed. Consequently, it was confirmed that even pollen attached to the surface of an air bubble had fertility.

Furthermore, an activator activating germination of pollen and elongation of the pollen tube may be added to an aqueous solution for producing an air bubble in the pollen supplying method according to the embodiment.

Experimental Case

Experiments for checking whether germination of pollen and elongation of the pollen tube are activated by adding an activator to an aqueous solution for producing an air bubble were performed.

Experimental Case 1

In an experimental case 1, first, an aqueous solution added with 10% sucrose, 5 ppm (=0.0005%) boric acid ($H_3BO_3$), 0.1 mM (mmol/l) magnesium sulfate heptahydrate ($MgSO_4 \cdot 7H_2O$), 1.0 mM calcium chloride ($CaCl_2$)), 1.0 mM potassium chloride (KCl), 0.8% gelatin, and 4 mg/ml pure pollen of *Pyrus bretschneideri* origin was produced and was filled in a foam spray container.

Further, in the experimental case 1, five foam spray containers in a state of being filled with the aqueous solution were kept at 25° C. for 0 hours, 12 hours, 24 hours, 48 hours, and 72 hours, respectively. Further, in the experimental case 1, five agar media each formed of 10% sucrose and 1% agarose were prepared, and microscopic air bubbles were discharged to a first agar medium from the foam spray container kept for 0 hours. Further, in the experimental case 1, microscopic air bubbles were discharged to a second agar medium from the foam spray container kept for 12 hours, and microscopic air bubbles were discharged to a third agar medium from the foam spray container kept for 24 hours. Further, in the experimental case 1, microscopic air bubbles were discharged to a fourth agar medium from the foam spray container kept for 48 hours, and microscopic air bubbles were discharged to a fifth agar medium from the foam spray container kept for 72 hours. Then, in the experimental case 1, pollen attaching to the surface of an air bubble was cultured (incubated) while keeping the five agar media at 25° C. for 12 hours, and the germination rate of pollen and the length of the pollen tube were observed and measured by use of a fluorescence microscope.

Sucrose, boric acid, magnesium sulfate heptahydrate, calcium chloride, potassium chloride, and gelatin manufactured by FUJIFILM Wako Pure Chemical Corporation were used as the additives to the aqueous solution. Further, sucrose and agarose also manufactured by FUJIFILM Wako Pure Chemical Corporation were used for forming an agar medium. Further, pure pollen of *Pyrus bretschneideri* origin manufactured by KOBAYASHI BAG MFG. CO., LTD was used. Further, foam spray containers manufactured by Seria Co., Ltd. were used. Furthermore, IX73 manufactured by Olympus Corporation was used as the fluorescence microscope.

Experimental Case 2

Further, in an experimental case 2, first, an aqueous solution added with 10% sucrose, 5 ppm boric acid, 0.1 mM magnesium sulfate heptahydrate, 1.0 mM calcium chloride, 1.0 mM potassium chloride, and 0.8% gelatin was produced and was filled in a foam spray container. Further, in the experimental case 2, pure pollen of *Pyrus bretschneideri* origin was filled in a powder spray container.

Further, in the experimental case 2, five powder spray containers in a state of being filled with the pure pollen of *Pyrus bretschneideri* origin were kept at 25° C. for 0 hours, 12 hours, 24 hours, 48 hours, and 72 hours, respectively. Further, in the experimental case 2, the same five agar media as those in the experimental case 1 were prepared, and microscopic air bubbles were discharged to each agar medium from the foam spray container. Further, in the experimental case 2, pollen was discharged to an air bubble in a first agar medium from the powder spray container kept for 0 hours, and pollen was discharged to an air bubble in a second agar medium from the powder spray container kept for 12 hours. Further, in the experimental case 2, pollen was discharged to an air bubble in a third agar medium from the powder spray container kept for 24 hours, pollen was discharged to an air bubble in a fourth agar medium from the powder spray container kept for 48 hours, and pollen was discharged to an air bubble in a fifth agar medium from the powder spray container kept for 72 hours. Then, in the experimental case 2, similarly to the experimental case 1, pollen attached to the surface of an air bubble was cultured while keeping the five agar media at 25° C. for 12 hours, and the germination rate of pollen and the length of the pollen tube were observed and measured by use of a fluorescence microscope.

Sucrose, boric acid, magnesium sulfate heptahydrate, calcium chloride, potassium chloride, and gelatin added to the aqueous solution, sucrose and agarose forming the agar medium, pure pollen of *Pyrus bretschneideri* origin, and the foam spray containers were the same as those in the experimental case 1. Further, commercially available powder spray containers purchased from Amazon Japan G. K. were used.

Comparative Case 1

In a comparative case 1, first, groups of pure pollen of *Pyrus bretschneideri* origin in a powdery state were kept at 25° C. for 0 hours, 12 hours, 24 hours, 48 hours, and 72 hours, respectively. Further, in the comparative case 1, the same five agar media as those in the experimental cases 1 and 2 were prepared; and the pollen kept for 0 hours was applied to a first agar medium with a spherical feather brush, and the pollen kept for 12 hours was applied to a second agar medium with the spherical feather brush. Further, in the comparative case 1, the pollen kept for 24 hours was applied to a third agar medium with the spherical feather brush, the pollen kept for 48 hours was applied to a fourth agar medium with the spherical feather brush, and the pollen kept for 72 hours was applied to a fifth agar medium with the spherical feather brush. Then, in the comparative case 1, similarly to the experimental cases 1 and 2, pollen was cultured while keeping the five agar media at 25° C. for 12 hours, and the germination rate of pollen and the length of the pollen tube were observed and measured by use of a fluorescence microscope.

Sucrose and agarose forming the agar medium and pure pollen of *Pyrus bretschneideri* origin were the same as those in the experimental case 1. Further, a commercially available spherical feather brush purchased from Amazon Japan G. K. was used.

Experimental Result

Figure 1:
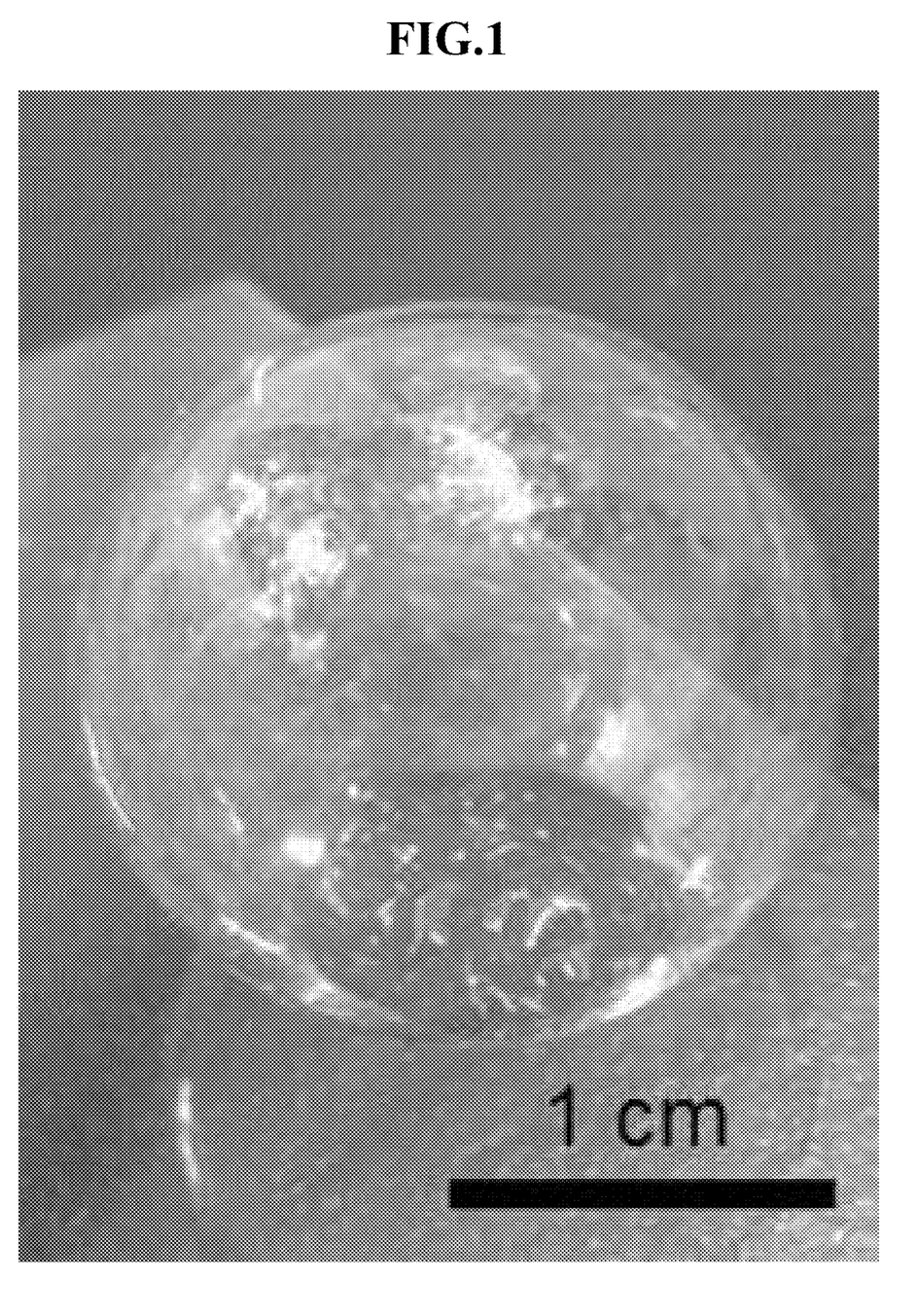
FIG. 1 is a diagram illustrating a state of placing an air bubble on a glass substrate in a pollen supplying method according to an embodiment of the present disclosure.
Figure 2:
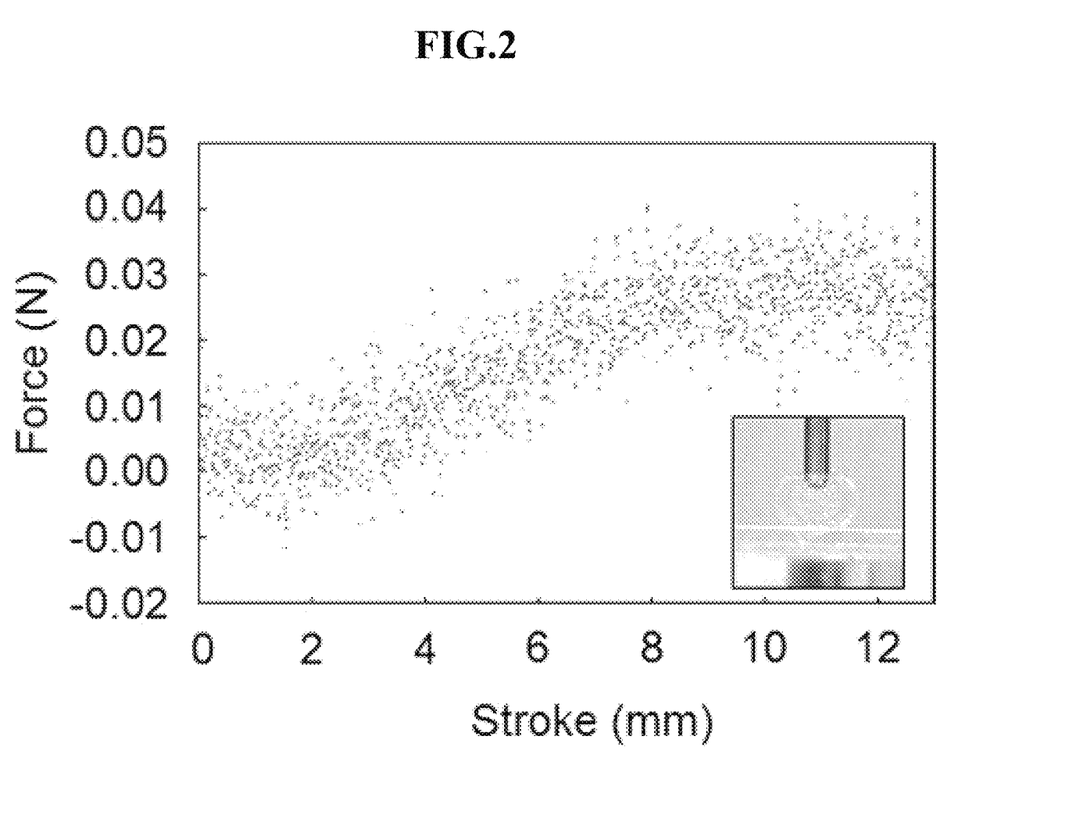
FIG. 2 is a graph illustrating measurement results of compressive stress of an air bubble by a compression tester.
Figure 3:
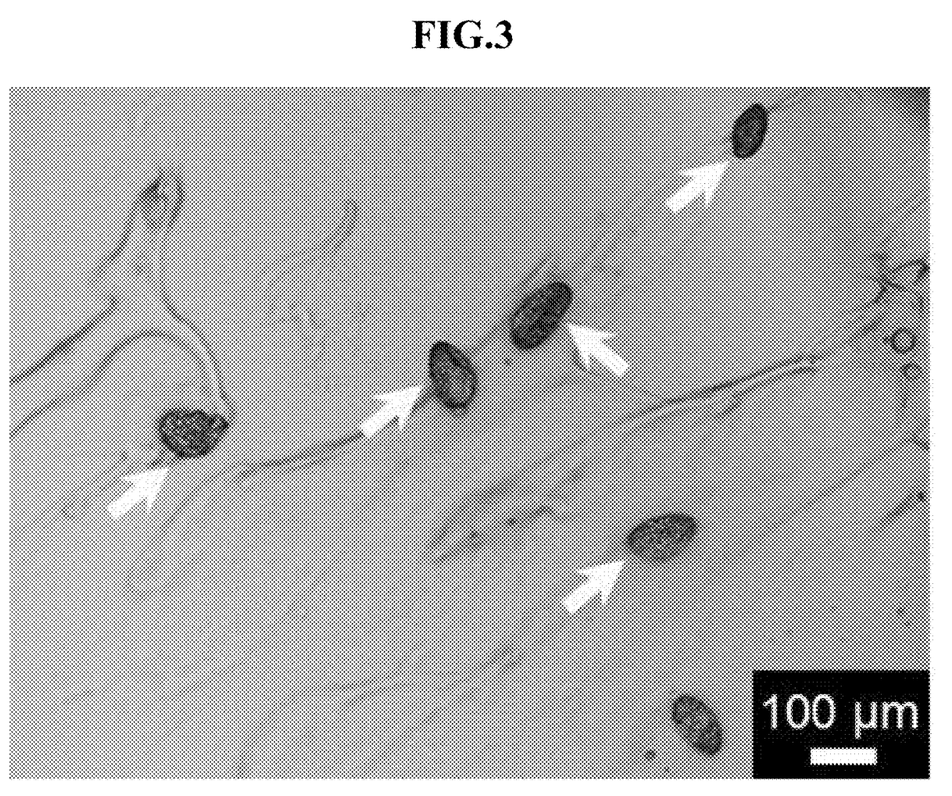
FIG. 3 is a diagram illustrating pollen dispersed in an air bubble observed by use of an optical microscope.
Figure 4A:
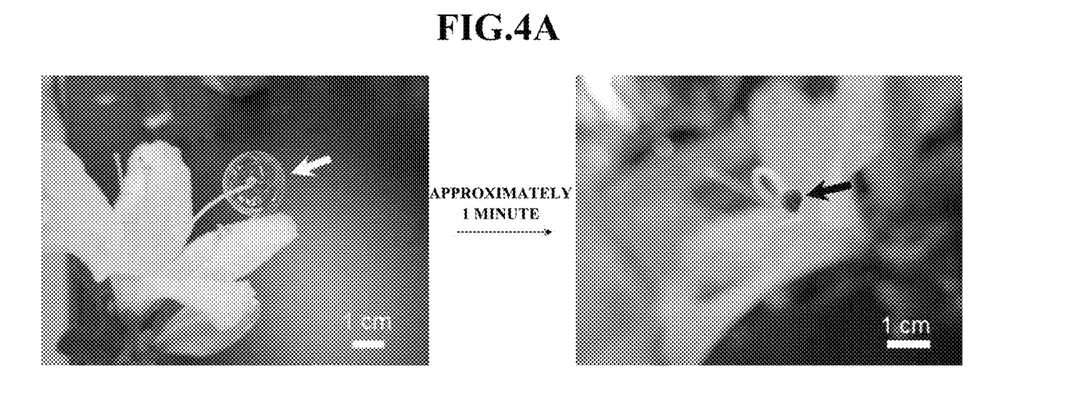
FIG. 4A is a diagram illustrating occurrence of a burst of an air bubble attached to a pistil of an azalea.
Figure 4B:
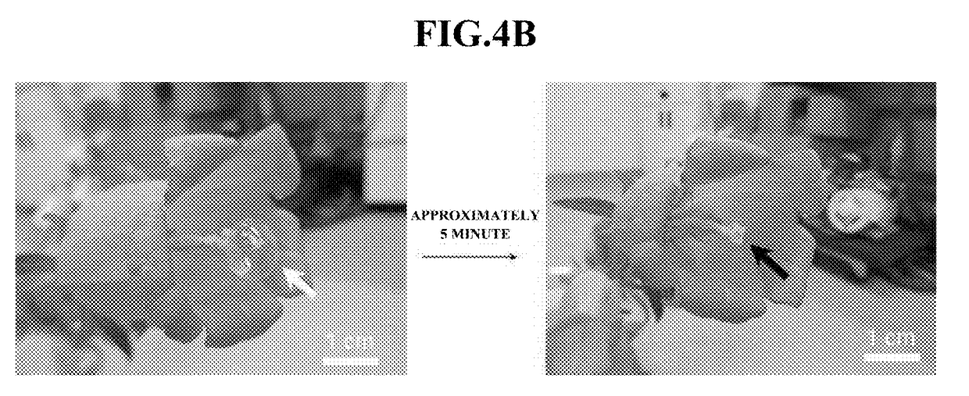
FIG. 4B is a diagram illustrating occurrence of a burst of an air bubble attached to a pistil of a campanula.
Figure 5A:
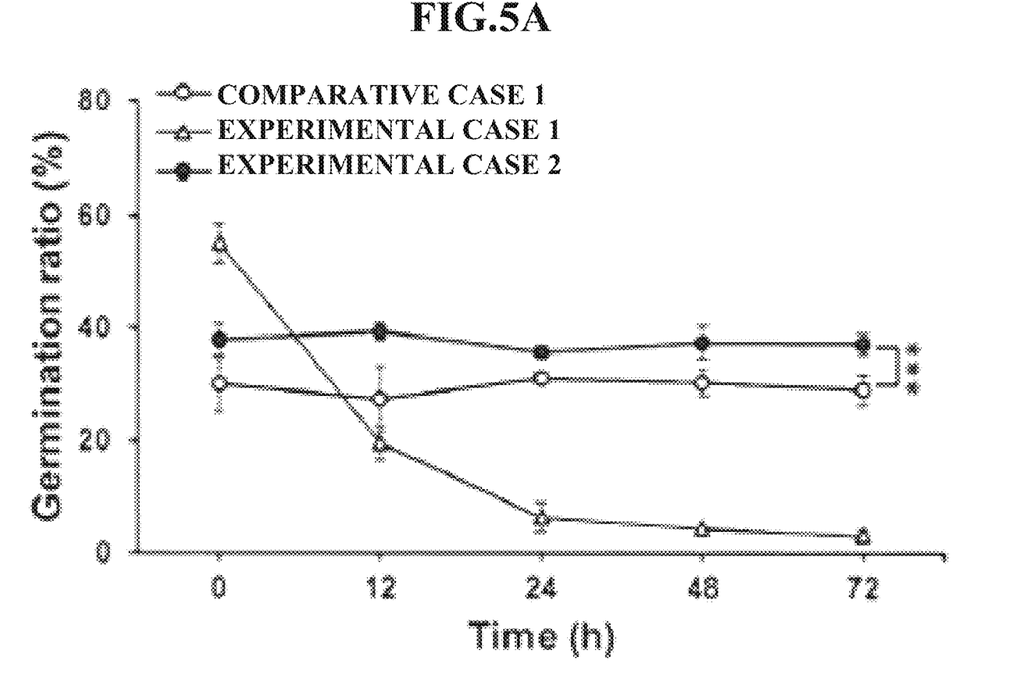
FIG. 5A is a diagram illustrating germination rates of pollen in experimental cases 1 and 2 and a comparative case 1.
Figure 5B:
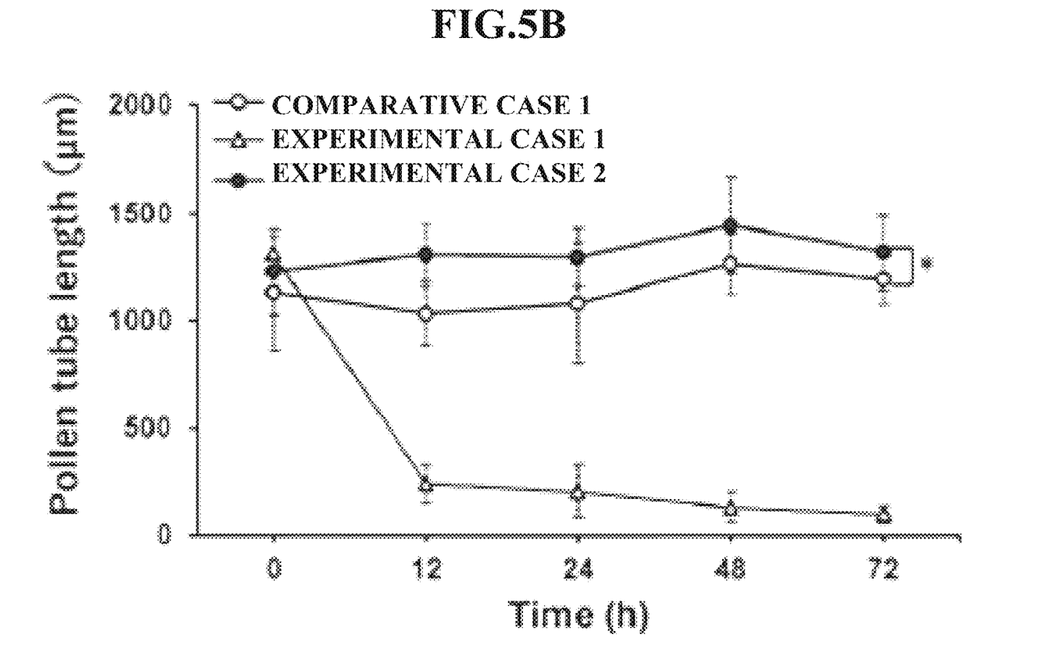
FIG. 5B is a diagram illustrating lengths of pollen tubes in the experimental cases 1 and 2 and the comparative case 1.
Figure 6:
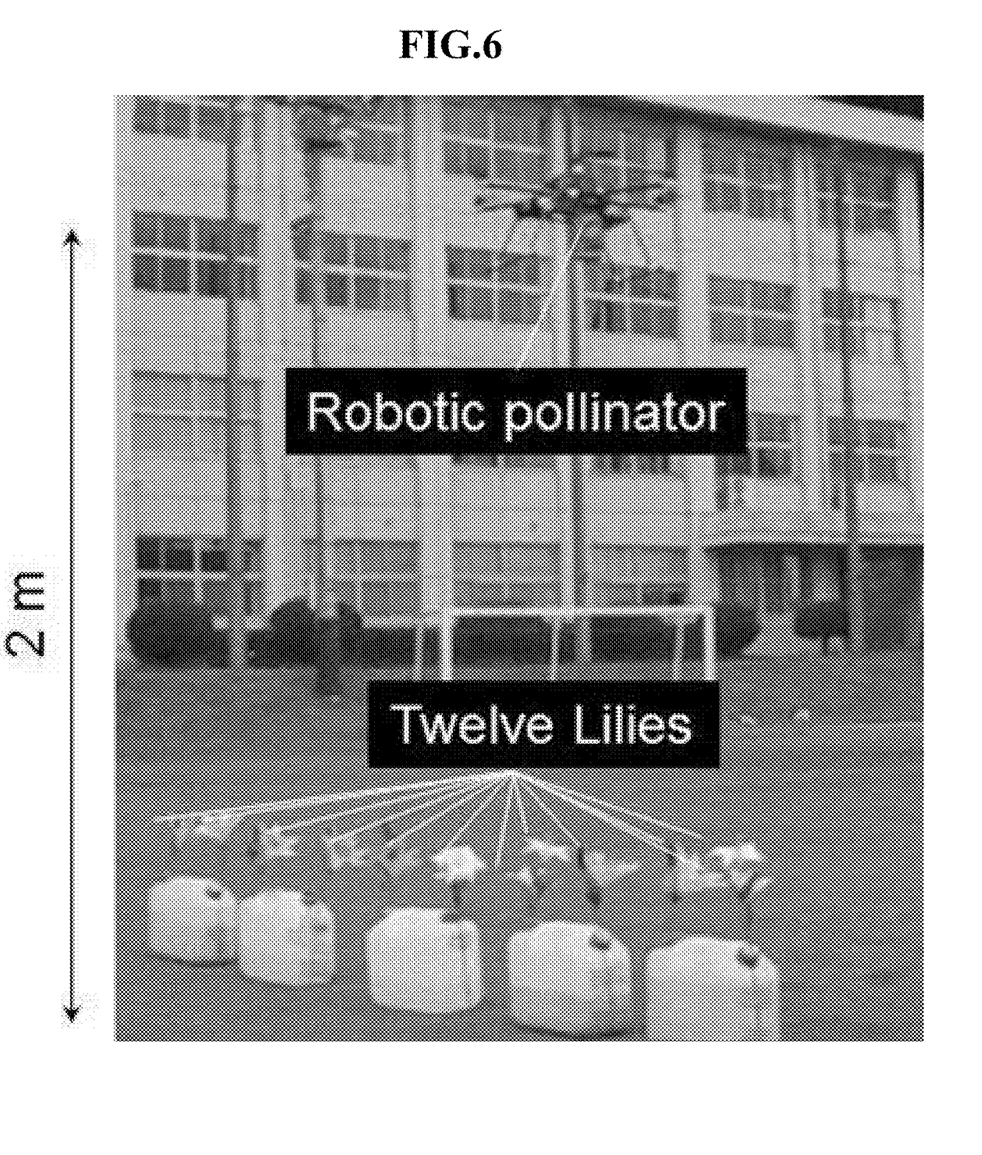
FIG. 6 is a diagram illustrating a state of spraying air bubbles by use of a drone.

As a result of the experiments, in the comparative case 1, germination rates of pollen and lengths of the pollen tubes respectively exhibited certain values regardless of the time for which the pollen was kept, as illustrated in FIG. 5A and FIG. 5B. Specifically, each germination rate of pollen exhibited approximately 30%, and the lengths of pollen tubes exhibited values ranging from 1000 to 1300 μm.

On the other hand, in the experimental case 1, the germination rate of pollen and the length of the pollen tube respectively exhibited values higher than those in the comparative case 1 when the time for which the pollen was kept was 0 hours, as illustrated in FIG. 5A and FIG. 5B. Specifically, the germination rate of pollen was approximately 55%, and the length of the pollen tube was approximately 1400 μm when the time for which the pollen was kept was 0 hours. However, in the experimental case 1, the germination rate of pollen and the length of the pollen tube respectively exhibited values lower than those in the comparative case 1 when the time for which the pollen was kept exceeded 12 hours. Specifically, the germination rate of pollen decreased to approximately 20% when the time for which the pollen was kept was 12 hours and further decreased to less than 10% when the time for which the pollen was kept was 24 hours, 48 hours, or 72 hours. Further, the length of a pollen tube decreased to less than 300 μm when the time for which the pollen was kept was 12 hours, 24 hours, 48 hours, or 72 hours.

On the other hand, in the experimental case 2, germination rates of pollen and lengths of the pollen tubes always exhibited values higher than those in the comparative case 1, respectively, regardless of the time for which the pollen was kept, as illustrated in FIG. 5A and FIG. 5B. Specifically, each germination rate of pollen was approximately 35%; and the lengths of pollen tubes exhibited values ranging from 1200 to 1500 μm and the values respectively exhibited about 10% higher than those in the comparative case 1.

As a result, it was confirmed that the aqueous solution used in the experimental cases 1 and 2 activates germination of pollen and elongation of the pollen tube. On the other hand, it was confirmed that when pollen was soaked in the aqueous solution used in the experimental cases 1 and 2 longer than at least 12 hours, the germination rate of pollen decreased, and the length of the pollen tube was short even when germination occurred.

It is assumed that the reason the germination rate of pollen decreased and the length of the pollen tube was short even when germination occurred when the time for which the pollen was kept exceeded 12 hours in the experimental case 1 is that heavy load was applied to a pollen particle due to osmotic pressure of the aqueous solution, and the pollen grain was damaged or burst.

While 10% sucrose was added to the aqueous solution in the experimental cases 1 and 2, sucrose may be added at any ratio without being limited to the above. However, it is preferable that sucrose in a range from 5 to 30% be added in order to be effective as a thickener and activator.

While 5 ppm boric acid was added to the aqueous solution in the experimental cases 1 and 2, boric acid may be added at any ratio without being limited to the above. However, it is preferable that boric acid in a range from 1 to 60 ppm be added in order to be effective as an activator.

While 0.1 mM magnesium sulfate heptahydrate was added to the aqueous solution in the experimental cases 1 and 2, magnesium sulfate heptahydrate may be added at any ratio without being limited to the above. However, it is preferable that magnesium sulfate heptahydrate in a range from 0.1 to 2.0 mM be added in order to be effective as an activator.

While 1.0 mM calcium chloride was added to the aqueous solution in the experimental cases 1 and 2, calcium chloride may be added at any ratio without being limited to the above. However, it is preferable that calcium chloride in a range from 0.1 to 2.0 mM be added in order to be effective as an activator.

While 1.0 mM potassium chloride was added to the aqueous solution in the experimental cases 1 and 2, potassium chloride may be added at any ratio without being limited to the above. However, it is preferable that potassium chloride in a range from 0.1 to 2.0 mM be added in order to be effective as an activator.

While 0.8% gelatin was added to the aqueous solution in the experimental cases 1 and 2, gelatin may be added at any ratio without being limited to the above. However, it is preferable that gelatin in a range from 0.2 to 2.0% be added in order to be effective as a thickener and activator.

Further, air bubbles may be released by an unmanned flying object such as a drone in the pollen supplying method according to the embodiment. In this case, it is preferable that the radius of an air bubble, the type and concentration of a thickener, and the like be adjusted according to how air bubbles are released by the unmanned flying object.

Air bubbles were released by an unmanned flying object, and whether an air bubble actually attaches to a pistil was checked. Specifically, as illustrated in FIG. 6, a commercially available soap bubble maker (Super Bubble Machine from Toysrus, Wayne, NJ, USA) was mounted on a drone (ACSL-PF1 manufactured by Autonomous Control Systems Laboratory Ltd.), and the drone was flown over 12 aligned artificial lily flowers at a constant speed; and an on-target rate of soap bubbles on the artificial flowers was measured. The soap bubble maker is specified to be capable of producing 5000 soap bubbles per minute, each bubble having a diameter of about 2 cm. Further, the drone is capable of autonomous flight using the Global Positioning System (GPS); and the drone was caused to autonomously fly at a flight altitude of 2 m and a speed of 2 m/s and was caused to pass over the artificial flowers once. Release of air bubbles by the drone was performed by Autonomous Control Systems Laboratory Ltd. under a windless condition. As a result of the measurement, the on-target rate of soap bubbles on the artificial flowers was approximately 83% (10/12=0.8333 . . . ).

As described above, the pollen supplying method according to the embodiment produces an air bubble with pollen attached to the surface thereof, releases the produced air bubble into the air, and attaches the air bubble to a pistil.

Thus, the pollen supplying method according to the embodiment enables pollination with a less amount of pollen than injecting an aqueous solution in which pollen is dispersed and enables supply of pollen without damaging a pistil. Consequently, the pollen supplying method according to the embodiment can efficiently supply pollen to a pistil of a plant even when an unmanned flying object such as a drone is used. Further, the pollen supplying method according to the embodiment can suppress scattering of pollen that may become an allergen.

Further, by supplying pollen with a flexible and light air bubble, the pollen supplying method according to the embodiment can reduce the possibility of damaging a stigma when pollen comes into contact with the pistil, can reliably perform pollination, and can suppress bearing of a malformed fruit. Further, even for a plant bearing an irregularly-shaped fruit without pollination of a plurality of stigmas, such as apple and pear, spherical air bubbles can equally come into contact with each stigma and therefore the pollen supplying method according to the embodiment facilitates simultaneous pollination of a plurality of stigmas.

Further, in the pollen supplying method according to the embodiment, an air bubble can take a diameter of any length adjusted to the size of a flower.

Thus, an air bubble can float in the air in a state of the surface area being enlarged compared with a waterdrop in which pollen is dispersed. Consequently, the probability of an air bubble coming into contact with a pistil increases, and the probability of an aqueous solution in which pollen is dispersed coming into contact with the pistil increases; and therefore pollination with a small amount of pollen can be achieved.

Further, in the pollen supplying method according to the embodiment, an aqueous solution used for producing an air bubble contains a surface-active agent.

Thus, the pollen supplying method according to the embodiment can produce a soap bubble with a diameter of any length adjusted to the size of a flower.

The surface-active agent is not limited to aforementioned sodium polyoxyethylene lauryl ether sulfate and may be another substance.

While a soap bubble is determined to have a diameter adjusted to the size of a flower in the embodiment, a plurality of microbubbles may be used as is the case in the experimental cases 1 and 2. In this case, for example, an air bubble may be brought into contact with a pistil by blowing a plurality of microbubbles to the pistil.

Thus, the pollen supplying method according to the embodiment can supply pollen with less damage to a pistil compared with a case of injecting an aqueous solution in which pollen is dispersed. Further, the pollen supplying method according to the embodiment can thus produce microbubbles without adding a surface-active agent to an aqueous solution. Consequently, the pollen supplying method according to the embodiment can provide the aforementioned effect regardless of whether a surface-active agent is added to an aqueous solution used for producing an air bubble.

Further, in the pollen supplying method according to the embodiment, an aqueous solution used for producing an air bubble contains a thickener raising viscosity.

Thus, in the pollen supplying method according to the embodiment, the time until a burst of an air bubble becomes longer; and therefore the probability of an air bubble coming into contact with a pistil increases, and the probability of an aqueous solution in which pollen is dispersed coming into contact with the pistil increases; and therefore pollination with a small amount of pollen can be achieved.

The thickener is not limited to aforementioned polyvinyl alcohol, sugar, honey, gelatin, starch powder, or sucrose and may be another substance.

Further, while it is preferable that an aqueous solution used for producing an air bubble contain a thickener in order to increase the time until a burst of an air bubble, the aqueous solution used for producing an air bubble may not contain a thickener.

Further, in the pollen supplying method according to the embodiment, the aforementioned activator may be added to an aqueous solution.

Thus, the pollen supplying method according to the embodiment can activate germination of pollen and elongation of the pollen tube after pollination.

The activator is not limited to aforementioned sucrose, boric acid, magnesium sulfate, calcium chloride, potassium chloride, and gelatin and may be another substance.

Further, while it is preferable that an activator be added to an aqueous solution used for producing an air bubble in order to activate germination of pollen and elongation of the pollen tube after pollination, an activator may not be added to the aqueous solution used for producing an air bubble.

Further, the pollen supplying method according to the embodiment produces an air bubble with pollen attached to the surface thereof when the air bubble is released, as described in the aforementioned experimental case 2, and pollen is preserved in a powdery state until being attached to the surface of an air bubble.

Thus, the pollen supplying method according to the embodiment can prevent pollen from being soaked in an aqueous solution for a long time. Consequently, decrease in the germination rate of pollen after pollination or delay in growth of a pollen tube after germination can be prevented.

While it is preferable that pollen be preserved in a powdery state until being attached to the surface of an air bubble in order to prevent the pollen being soaked in an aqueous solution for a long time, an air bubble may be produced in a state of pollen being dispersed in an aqueous solution.

Further, the pollen supplying method according to the embodiment can blow pollen to a previously produced air bubble and attach the pollen to the air bubble, as described in the aforementioned experimental case 2.

Thus, the pollen supplying method according to the embodiment can attach pollen to the surface of an air bubble immediately before bringing the air bubble into contact with a pistil and can prevent the pollen from being soaked in an aqueous solution for a long time.

While an air bubble with pollen attached to the surface thereof is produced by bringing pollen into contact with an air bubble without pollen attached to the surface thereof in the aforementioned experimental case 2, an air bubble with pollen attached to the surface thereof may be produced by bringing an air bubble without pollen attached to the surface thereof into contact with pollen. For example, pollen may be attached to the surface of an air bubble by blowing a produced air bubble to pollen provided at a predetermined position in advance.

Thus, the pollen supplying method according to the embodiment can attach pollen to the surface of an air bubble immediately before bringing the air bubble into contact with a pistil and can prevent the pollen from being soaked in an aqueous solution for a long time.

Further, in the pollen supplying method according to the embodiment, an air bubble attaching to a pistil bursts by water given by the pistil.

Thus, in the pollen supplying method according to the embodiment, an aqueous solution in which pollen is dispersed can be sprayed in close proximity to a pistil, and a part of the aqueous solution not in direct contact with the pistil contributes to pollination; and therefore pollination with a small amount of pollen can be achieved.

While it is preferable for spraying an aqueous solution in which pollen is dispersed in close proximity to a pistil that an air bubble attaching to the pistil burst by water given by the pistil, pollen can be supplied to the pistil from a contact part between the air bubble and the pistil even when an air bubble attaching to the pistil does not burst by water given by the pistil.

Further, the pollen supplying method according to the embodiment can release an air bubble by use of an unmanned flying object.

Thus, the pollen supplying method according to the embodiment can reliably and simply supply pollen to a pistil across a wide range.

While it is preferable for reliably and simply supplying pollen to a pistil across a wide range that an air bubble be released by an unmanned flying object, for example, a human may release an air bubble toward a pistil, without being limited to the above.

The foregoing describes some example embodiments for explanatory purposes. Although the foregoing discussion has presented specific embodiments, persons skilled in the art will recognize that changes may be made in form and detail without departing from the broader spirit and scope of the invention. Accordingly, the specification and drawings are to be regarded in an illustrative rather than a restrictive sense. This detailed description, therefore, is not to be taken in a limiting sense, and the scope of the invention is defined only by the included claims, along with the full range of equivalents to which such claims are entitled.

This application claims the benefit of Japanese Patent Application No. 2018-216647, filed on Nov. 19, 2018, the entire disclosure of which is incorporated by reference herein.

INDUSTRIAL APPLICABILITY

The pollen supplying method according to the present disclosure can efficiently supply pollen to a pistil of a plant even when an unmanned flying object such as a drone is used and therefore is useful in, for example, fruit growing and horticulture.

The invention claimed is:

1. A pollen supplying method for supplying pollen to a pistil of a plant, the method comprising:

an air bubble production step of producing an air bubble using an aqueous solution and attaching a pollen in a powdery state to an exterior surface of the air bubble; and an air bubble attachment step of releasing the produced air bubble into air and attaching the air bubble to the pistil, wherein in the air bubble production step, the air bubble with the pollen attached to the exterior surface thereof is produced, when the air bubble is released in the air bubble attachment step, and the pollen is preserved in a powdery state for at least 12 hours in a container until being attached to the exterior surface of the air bubble; wherein the pollen supplying method reduces possible damage to a stigma when the pollen comes in contact with the pistil.

2. The pollen supplying method according to claim 1, wherein the air bubble is a sphere with a diameter of any length.

3. The pollen supplying method according to claim 2, wherein the aqueous solution used for producing the air bubble contains a surface-active agent.

4. The pollen supplying method according to claim 1, wherein the aqueous solution used for producing the air bubble contains a thickener raising viscosity.

5. The pollen supplying method according to claim 4, wherein the aqueous solution is added with at least sucrose, boric acid, magnesium sulfate, calcium chloride, potassium chloride, and gelatin.

6. The pollen supplying method according to claim 1, wherein the aqueous solution used for producing the air bubble contains a substance activating germination of the pollen and elongation of a pollen tube.

7. The pollen supplying method according to claim 1, wherein in the air bubble production step, the air bubble with the pollen attached to the exterior surface thereof is produced by discharging the pollen toward an air bubble free of pollen on the exterior surface thereof to bring the pollen into contact with the air bubble and attach to the exterior surface of the air bubble.

8. The pollen supplying method according to claim 1, wherein in the air bubble production step, the air bubble with the pollen attached to the exterior surface thereof is produced by blowing an air bubble free of pollen on the exterior surface thereof toward pollen at a predetermined position to bring the air bubble into contact with the pollen which then attaches to the exterior surface of the air bubble.

9. The pollen supplying method according to claim 1, wherein the air bubble bursts by water given by the pistil.

10. The pollen supplying method according to claim 1, wherein in the air bubble attachment step, the air bubble is released by use of an unmanned flying object.

* * * * *